(12) United States Patent
Deresiewicz et al.

(10) Patent No.: US 6,548,552 B1
(45) Date of Patent: *Apr. 15, 2003

(54) ABSORBENT ARTICLE, PARTICULARLY A TAMPON HAVING ADDITIVES THAT REDUCE TOXIC SHOCK SYNDROME TOXIN PRODUCTION

(75) Inventors: Robert L. Deresiewicz, Newton, MA (US); Dennis L. Kasper, Newton, MA (US)

(73) Assignee: The Brigham and Women's Hospital, Inc., Boston, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/150,373

(22) Filed: Sep. 10, 1998

Related U.S. Application Data

(60) Provisional application No. 60/058,616, filed on Sep. 11, 1997, now abandoned.

(51) Int. Cl.[7] ..................... A61K 31/095; A61K 31/00; A61F 13/00; A61L 15/16
(52) U.S. Cl. .................. 514/706; 424/431; 424/443; 424/445; 424/446; 424/447; 514/529; 514/546; 514/557; 514/562; 514/665; 514/666; 514/676; 514/715; 514/722; 514/723; 514/724; 514/738; 514/975
(58) Field of Search ................................ 514/474, 458, 514/706, 562, 738, 975, 461, 529, 546, 557, 715, 722, 723, 724, 728, 731, 665, 666, 676; 424/431, 434, 443, 445, 446, 447, 711

(56) References Cited

U.S. PATENT DOCUMENTS

| | | | |
|---|---|---|---|
| 4,722,937 A | * 2/1988 | Jacob et al. ................ | 514/474 |
| 5,346,468 A | 9/1994 | Campion et al. ............ | 604/13 |
| 5,364,383 A | 11/1994 | Hayes et al. ................ | 604/384 |
| 5,417,224 A | * 5/1995 | Petrus et al. ................ | 128/833 |
| 5,547,985 A | 8/1996 | Brown-Skrobot et al. .. | 514/546 |
| 5,558,631 A | 9/1996 | Campion et al. ............ | 604/13 |
| 5,612,045 A | 3/1997 | Syverson .................... | 424/402 |
| 5,641,503 A | * 6/1997 | Brown-Skrobot ........... | 424/431 |

FOREIGN PATENT DOCUMENTS

| | | | |
|---|---|---|---|
| EP | 0 483 835 | * | 5/1992 |
| WO | WO 87/04069 | | 7/1987 |
| WO | 96/40300 | * | 12/1996 |

OTHER PUBLICATIONS

Geshnizgani, et al., "Defined Medium Simulating Genital Tract Secretions for Growth of Vaginal Microflora," *J. Clin. Microbiol.* 30:1323–1326 (1992).

Kreiswirth, et al., "Toxic Shock Syndrome Toxin 1 Is Encoded by a Variable Genetic Element," *Rev. Infect. Dis.* 11:S83–S89 (1989).

* cited by examiner

*Primary Examiner*—Michael G. Hartley
*Assistant Examiner*—Frank Choi
(74) *Attorney, Agent, or Firm*—Michael A. Sanzo; Fitch, Even, Tabin & Flannery

(57) ABSTRACT

An absorbent article, particularly a tampon having additives that reduce toxic shock syndrome toxin (TST-1) production is disclosed. The tampon has a combination of an effective amount of at least one oxygen inhibiting agent and an effective amount of at least one surface active agent applied to: the surface of the absorbent tampon material; the surfaces of the fibers comprising the tampon; to the tampon applicator; or any combination of the foregoing. The effective amounts of the oxygen inhibiting agent and the surface active agent are sufficient to reduce the toxin production at lease about 50%, but do not negatively affect the wearer's normal vaginal flora.

17 Claims, No Drawings

ABSORBENT ARTICLE, PARTICULARLY A TAMPON HAVING ADDITIVES THAT REDUCE TOXIC SHOCK SYNDROME TOXIN PRODUCTION

CROSS REFERENCE TO RELATED APPLICATIONS

The present application claims priority to U.S. provisional application No. 60/058,616, filed on Sep. 11, 1997 (now abandoned).

FIELD OF THE INVENTION

This invention relates to an absorbent article, particularly a tampon having additives that reduce toxic shock syndrome toxin (TSST-1) production.

BACKGROUND OF THE INVENTION

Efforts to inhibit the production of toxic shock syndrome toxin (TSST-1) production are described in U.S. Pat. Nos. 5,547,985 and 5,612,045. However, certain additives, while reducing toxic shock syndrome toxin production, will negatively impact the wearer's vaginal flora. Therefore, a need exists to provide a tampon having additives that will reduce toxic shock syndrome toxin (TSST-1) production without adversely affecting the normal vaginal flora or, if applied as a bandage, the normal flora at the relevant body site.

SUMMARY OF THE INVENTION

This invention relates to an absorbent article, particularly a tampon having additives that reduce toxic shock syndrome toxin (TSST-1) production without adversely affecting a woman wearer's vaginal flora.

In one preferred embodiment, this invention relates to a tampon that has a combination of at least one oxygen inhibiting agent and at least one surface active agent or humectant selected from a specific group applied thereto. The terms "oxygen inhibiting agent" or "oxygen inhibitor," as used herein refer to: a reducing agent, a free radical scavenger, an antioxidant or some other agent that reduces the amount of oxygen within a tampon. Particularly preferred oxygen inhibiting agents for use in the present invention include: ascorbic acid, vitamin E, N-acetylcysteine, and beta-mercaptoethanol. The surface active agent can comprise surfactants, which include, but are not limited to Tween 20™ (Polysorbate 20). In an alternative preferred embodiment of the present invention, the surface active agent may be replaced by glycerin (glycerol), a humectant. The reducing agent and surface active agent can be applied to: the surface of the absorbent tampon material; the surfaces of the fibers comprising the tampon; to the tampon applicator; or any combination of the foregoing. It is believed that oxygen inhibiting agents and surfactants or humectants interfere with the production of TSST-1 by at least two different mechanisms, thereby enhancing the effectiveness of the combination over that of either class alone.

The present invention also relates to a composition of matter for adding to an absorbent article to reduce toxic shock syndrome toxin (TSST-1) production, and to a method for reducing toxic shock syndrome toxin (TSST-1) production.

DETAILED DESCRIPTION OF THE INVENTION

This invention relates to an absorbent article, particularly a tampon that has additives that reduce toxic shock syndrome toxin (TSST-1) production without adversely affecting the normal vaginal flora or normal flora elsewhere where other types of absorbent articles may be applied.

There exists in the female body a complex process which maintains the vagina and physiologically related areas in a healthy state. In a female between the age of menarche and menopause, the normal vagina provides an ecosystem for a variety of microorganisms. Bacteria are the predominant type of microorganism present in the vagina. Most women harbor about $10^9$ bacteria per gram of vaginal exudate. The bacterial flora of the vagina is comprised of both facultative and anaerobic bacteria. The more commonly isolated bacteria are Lactobacillus species, Corynebacteria species, *Gardnerella vaginalis*, Staphyloccus species, Peptococcus species, facultative and anaerobic streptococcal species, and Bateroides species.

Vaginal tampons suitable for use in this invention are usually made of absorbent fibers, including natural and/or synthetic fibers, compressed into a unitary body of a size which may easily be inserted into the vaginal cavity. They are normally made in an elongated cylindrical form in order that they may have a sufficiently large body of material to provide the required absorbing capacity, but may be made in a variety of shapes. The tampon may or may not be compressed, although compressed types are now generally preferred. The tampon may be made of various fiber blends including both absorbent and nonabsorbent fibers, which may or may not, have a suitable cover or wrapper.

The tampon used in the present invention is not limited to any particular configuration. Particularly preferred tampons suitable for use in carrying out the present invention are those manufactured by Tambrands, Inc. of White Plains, N.Y. Patent publications describing tampons suitable for use in carrying out the present invention include: U.S. Pat. No. 5,364,383. Patent publications describing applicators suitable for use in carrying out the present invention are described in U.S. Pat. Nos. 5,346,468 and 5,558,631.

In one preferred embodiment, this invention relates to a tampon that has a combination of at least one oxygen inhibiting agent and at least one surface active agent or humectant selected from a specific group applied thereto. The terms "oxygen inhibiting agent" or "oxygen inhibitor," as used herein refer to: a reducing agent, a free radical scavenger, an antioxidant, or some other agent that displaces oxygen from within the tampon. Antioxidants include natural and synthetic antioxidants. Four common synthetic antioxidants comprise: butylated hydroxyanisole (BHA), butylated hydroxytoluene (BHT), propyl gallate (PG), and tertiary butylhydroquinone (TBHQ). Natural antioxidants include mixed tocopherols, citric acid, ascorbic acid (vitamin C), ascorbyl palmitate, and erythorbic acid. Other antioxidants include: thiodipropionic acid and salts, sodium and potassium bisulfite, sodium sulfite, and sodium and potassium metabisulfite. Particularly preferred oxygen inhibiting agents for use in the present invention include: ascorbic acid, vitamin E, and N-acetylcysteine. Additionally, materials may be added which exhibit both the properties of oxygen inhibiting agents and surfactants, N-acetylcysteine is a preferred example. The present invention, however, is not limited to the foregoing list of oxygen inhibiting agents.

The term "surface active agents", as used herein, refers to classes of chemical compounds commonly called surfactants and humectants. Surfactants for the purposes of this invention may include, but are not limited to: TWEEN 20™ (polysorbate 20), TWEEN 40™ (polysorbate 40), TWEEN 60™ (polysorbate 60), TWEEN 80™ (polysorbate 80), PPG-5-laureth-5, PEG-8 stearate, PEG 200 ML, polyethylene glycol, polypropylene glycol, and other glycols, Laureth-3, Laureth-4, sodium laureth sulfate, disodium laureth sulfosuccinate. Tween 20 is a particularly preferred surface active agent for use in this present invention.

In an alternative and preferred embodiment of the present invention, the surface active agent may be replaced by glycerin, a humectant. In still another embodiment, both glycerin and Tween 20 may be used with one or more oxygen inhibiting agent(s).

The compositions of the present invention can be prepared and applied in any suitable form, but are preferably prepared in forms including, without limitation aqueous solutions, lotions, balms, gels, salves, ointments, boluses, suppositories, and the like. The compositions may be applied to the absorbent article using conventional methods for applying an inhibitory agent to the desired absorbent article. For example, depending on their characteristics, the compositions may be sprayed onto the absorbent article, or the absorbent article may be dipped in a liquid bath having the agent therein, and then air dried. The compositions of the present invention are not restricted to use with tampons, but may also be used with other wound salves or dressings, particularly nasal packings and other surgical dressings.

The oxygen inhibiting agent and surface active agent can be applied to the tampon separately, or combined and then applied to the tampon. The oxygen inhibiting agent and the surface active agent (surfactant or humectant) can be applied to: the surface of the absorbent tampon material; the surfaces of the fibers comprising the tampon; to the tampon applicator; or any combination of the foregoing. If the oxygen inhibiting agent and surface active agent are applied to the tampon applicator, these substances should be applied to either a portion of the applicator that will contact the user's body, a portion of the applicator that will transfer the substances to the tampon, or both.

It has been found that ascorbic acid can reduce toxin production by up to about 40%, but does not inhibit Staphylococcal growth. It has also been found that certain surface active agents, e.g., surfactants, can also reduce toxin production without inhibiting bacterial growth. Without wishing to be bound by any particular theory, it is believed that the surfactants may interfere with TSST-1 production by staphylococci by blocking the transduction of the environmental signal that triggers TSST-1 production across the bacterial cell membrane. Oxygen inhibiting agents, on the other hand, may work by limiting Staphylococcal access to $O_2$ or to some metabolite of $O_2$, of which at least one of those molecular species appears necessary for TSST-1 production. The reduction in TSS toxin production and the effect of the composition on the wearer's vaginal flora can be measured as described in the Test Methods (Example 4) section of this specification.

In a particularly preferred embodiment, the combination of the oxygen inhibiting agent and surface active agent causes at least about a 50% reduction in toxin production as measured by reporter gene fusion in vitro. More preferably, the combination of the oxygen inhibiting agent and surface active agent causes a reduction in toxin production in an in vitro laboratory test in the following amounts in ascending order of preference, at least about: 75%, 90%, and 99%. Still more preferably, it is desired for the combination of the oxygen inhibiting agent and the surface active agent to cause reduction in toxin production in the above amounts when the tampon is worn.

The oxygen inhibiting agent and the surface active agent can be applied in any suitable concentration (that is, an effective amount) which results in a reduction in TSS toxin production, but which does not negatively affect the wearer's normal vaginal flora.

The invention will be illustrated by the following Examples, but the invention is not limited thereto and is fully applicable to the full disclosure.

EXAMPLES

Example 1

Compositions Containing Surface Active Agent and N-acetylcysteine

A composition of matter for adding to an absorbent article to reduce toxic shock syndrome toxin (TSST-1) production without adversely impacting the normal vaginal flora (or if the absorbent article is not a tampon, the normal flora at the body sites where the absorbent article is applied) is prepared using 10 mM N-acetylcysteine as the oxygen inhibiting agent, and 0.2% Tween 20™ (polysorbate 20) as the surface active agent. The effective amounts of the oxygen inhibiting agent and the surface active agent are sufficient to reduce the toxin production at least about 50% in in vitro testing.

Without wishing to be bound to any particular quantities, it is believed that effective concentrations of glycerol are between about 0.2% and about 0.6% per amount of body fluid present (e.g., in the tampon). Therefore, if 1 gram of body fluid is present, an effective amount is believed to be greater than or equal to about 0.002 grams of available glycerol. If 20 grams of body fluid are present, an effective amount is believed to be up to about 0.12 grams which would combine to yield a range of between about 0.002 grams and about 0.12 grams. Effective concentrations of Tween 20 are believed to be between about 0.1% and 0.2%. Effective concentrations of vitamin C are believed to between about 0.015% and about 0.25%. Effective concentrations of N-acetylcysteine are believed to be between about 5 mM up and about 10 mM per gram of absorbed fluid.

Example 2

Tampon Treated With Surface Active Agent and an Inert Gas

Another embodiment of this invention is a tampon coated with 0.2% Tween 20 based on the expected maximum absorbency of the tampon. The free and available oxygen within the tampon is displaced by nitrogen gas and the tampon is then sealed in a thin metallic foil and placed within the tampon inserter, such that, upon insertion, the force on the inserter rod pushes the tampon out of the metallic wrapper and deposits it in the vagina.

Example 3

Tampon Treated With Glycerol and Delta-Tocopherol

Yet another embodiment of this invention adds about 0.02 grams of glycerol to the outside surface of the tampon inserter which contacts the vaginal tissues during insertion, and the tampon is coated with approximately 0.30 g of delta-tocopherol.

Example 4

Test Methods

A. Determination of Effect of Test Compounds on TSST-1 Production by *S. aureus*

Staphylococcal reporter strains were created to measure the impact of various test material on TSST-1 toxin production. Each reporter strain is derived from a different TSST-1-producing clinical *S. aureus* isolate and each contains a fusion of the promoter of the gene encoding TSST-1 (tst) in that strain with an *E. coli* lacZ gene (encoding beta-galactosidase), integrated in single copy on the chromosome. The clinical strains used were MN8 (see U.S. Pat. No. 5,612,045), RN5038, RN4435, RN5719 (Kreiswirth, et al., Rev. Infect. Dis. 11 (supp.1) 583–588 (1989)) and SA101.

In order to create the reporter strains, an approximately 355 base-pair polynucleotide sufficient for promoter activity was, in each case, cloned from the genomic DNA immediately upstream of tst in that strain. The polynucleotide was inserted into the multiple cloning site (mcs) of shuttle plasmid pJFKL100. pJFKL100 is an integrative shuttle plasmid derived from plasmid pRB318 (Bruckner, *Gene* 122:187–92 (1992)) by deletion of the gram positive ori, and insertion if ermC from plasmid pMIN164 (Hovde, et al., *Mol. Gen. Genet.* 220:324–33 (1990)) and attP from phage L54 alpha (Lee, et al., *J Bacteriol.* 171:1652–7 (1989)). The pJFKL100 MCS is adjacent to the $S^1$ end of lacZ; cloning into it creates translational fusions between the cloned DNA and lacZ. The MCS-LacZ cassette is flanked on either end by transcriptional terminators to prevent spurious read-through from nearby DNA.

Once constructed, the lacZ fusions were integrated in single copy into the *S. aureus* geh gene (encoding glycerol ester hydrolase) in strain CYL316 (Lee, et al., *Gene* 106:101–5 (1991)). From there, the chromosomal fusions were moved into the target *S. aureus* strain by transduction with phage 80 alpha. All final constructs were verified by lipase assay, erythromycin resistance testing, and Southern blotting, probing both with a geh clone, and with pJFKL100.

During development of the system, the fidelity of such reporter constructs in predicting TSST-1 production was verified under a variety of physiological and environmental conditions. Since the reporter fusions are inserted into geh, the native tst gene is undisturbed in each case, and continues to function. Thus, beta-galactosidase reporter activity can be directly compared to TSST-1 production in a single reporter strain under any particular test condition. Conditions tested included the effects of varying the growth media in which the cells are grown prior to testing, the effects of the stage of growth in batch culture at which the assay is performed, and the impact of the quantity of oxygen available to the growing culture. In all cases tested, the measured amount of beta-galactosidase activity was in good agreement with the measured amount of TSST-1.

Each surfactant is tested against three different reporter strains. The strains are grown overnight at 37 degrees C., 250 RPM in brain-heart infusion either alone or with various concentrations of each surfactant. The next day, serial determinations of optical density are made to establish that each culture has reached saturation. Aliquots of cells are collected and their beta-galactosidase contents determined using a chemiluminescent substrate. Results are reported either as relative light units (RLU; the raw output from the assay) or as units of beta galactosidase (by comparison to a standard curve constructed with pure beta-galactosidase), and are normalized for the optical density of each culture.

Controls: A standard curve using pure beta-galactosidase is run in parallel with each experiment. In addition, a portion of each saturated control culture (no added surfactant) is mixed with surfactant and assayed, in order to establish that the presence of each surfactant does not spuriously affect the beta-galactosidase assay.

The beta-galactosidase assay is performed with the Galacto-Light-Plus Kit (Tropix, New Bedford, Mass.) according to the following protocol, modified from the Tropix literature for optimal performance in *S. aureus:*

Approximately $1.5 \times 10^9$ staphylococcal cells (e.g., 500 µl of a culture whose undiluted $OD_{540}$ is 8.0) are collected in a 1.5 ml eppendorf tube, washed with phosphate-buffered saline (PBS), and resuspended in 400 µl ice-cold Lysis Solution 1.0 mM dithiothreitol (DTT)+0.01% bovine serum albumin (BSA). Lysis Solution is a component of the Galacto-Light-Plus Kit. To the cell suspension is added about 0.3 cc acid-washed glass beads, and the mixture is vortexed at high power, 4° C., for 8 min. (Glass beads of diameters ranging from 425–600 µm are used. Beads should be prepared by soaking them in 0.1 M HCl overnight; flushing them extensively with water until the pH of the wash water is at least 7.0; and then baking them in a glass beaker at 200° C. for 4 hours. Once prepared, the beads can be stored indefinitely.) The cell lysis mixture is centrifuged at 4° C. for 4 minutes, and the supernatant fluid is retained. This supernatant is termed "cell extract," and contains the beta-galactosidase activity that is to be measured.

Three µl of each cell extract is combined with 7 µl of Lysis Solution in eppendorf tubes, in triplicate. 100 µl of Reaction Buffer is added to each tube. (Reaction Buffer is Galacton-Plus substrate diluted 1:100 in Galacto-Light Reaction Buffer Diluent. Both are components of the Galacto-Light-Plus kit. The Reaction Buffer should be made up fresh, in bulk, just before use.) The tubes are incubated at 20° C. for 60 minutes. During this time, the beta-galactosidase that has been liberated from the *S. aureus* cells cleaves the Galacton-Plus chemiluminescent substrate. The first cleavage product, which is not chemiluminescent, has a long half-life at the pH at which this reaction is conducted. After the incubation is completed, 73.3 µl of the reaction mixture is transferred from the eppendorf tube to a luminometer cuvette containing 10 µl of 16.7 mM PETG. The final concentration of PETG in the mixture is thus 2 mM, a concentration which completely inhibits further beta-galactosidase activity. (PETG is phenyl-ethyl-thiogalactopyranoside, a competitive inhibitor of beta-galactosidase. It may be purchased from Molecular Probes, Eugene, OR).

To measure the amount of product that has been generated by the beta-galactosidase, a luminometer should be set (e.g., Monolight 2010, Analytical Luminescence Laboratory, Cockeysville, Md.) to inject 100 µl of Accelerator Solution (a component of the Galacto-Light-Plus kit) into the cuvette, to wait 5 seconds, and then to measure luminescence for 5 seconds. Each sample is then injected and measured in turn. Accelerator changes the pH in the vessel thereby rendering the first cleavage product unstable. That product breaks down and, in the process, releases a photon. The amount of light measured is thus an indicator of the amount of beta-galactosidase activity that was present in the cell extract.

With each experiment, a standard curve should be generated using *E. coli* beta-galactosidase (e.g., from Sigma Chemical Co., St. Louis, Mo.). To prepare a working stock of beta-galactosidase, the enzyme may be diluted to 10 units/ml in 0.1 M sodium phosphate, 1.0% BSA, pH 7.0. The standard curve may be generated by mixing 2 µl beta-galactosidase (at concentrations ranging from $1 \times 10^4$ to 10 U/ml), 3 µl cell extract from a beta-galactosidase-negative strain of *S. aureus* (e.g., RN6390), and 5 µl lysis solution. 3 µl of the mixture may then be used in the assay, as detailed above. The standard curve should be used to assess the linear range of the assay and to convert the relative light units measured by the luminometer to units of beta-galactosidase activity.

B. Determination of the Effect of Various Test Materials on Growth of *S. aureus*

Prior and in parallel with beta-galactosidase reporter testing, the impact of various test materials on *S. aureus* growth in batch culture was determined. *S. aureus* reporter strains were grown in BHI (Brain-Heart Infusion media) with or without test additives as described above. Final optical densities at 540 nm ($OD_{540}$) of each culture within a given experiment were compared. In some cases, addition of the test material(s) did not alter the final $OD_{540}$ up to the highest concentration tested. In other cases, higher concentrations of test material(s) did impact the final OD540 of the culture. In certain cases, yield of biomass per volume of culture was used as a supplementary way of assessing staphylococcal growth.

C. Determination of Effect of Various Fiber Finishes on Vaginal Microflora

Compounds used in the manufacturing and processing of tampon fibers are added at concentrations of 1, 10, and 100 mM to a chemically defined medium (VDM) simulating vaginal tract secretions (See reference 1 in Section C below). These compounds included Polysorbate 20 (e.g., Tween 20™) and glycerin. Tubes containing 10 ml of VDM plus the test additives are inoculated with the following isolates: *Candida albicans., Corynebacterium striatum,* Enterococcus sp., *Escherichia coli, Lactobacillus acidophilus, Peptostreptococcus anaerobius, Prevotella bivia, Staphylococcus aureus,* or *Staphylococcus epidermidis.* Bacterial counts are determined following 24 and 48 hours of incubation under the appropriate atmospheric condition for each isolate to be tested.

The various concentrations of glycerin tested did not effect the growth of the isolates tested, with the exception of *P. bivia* which was inhibited at the 100 mM concentration. Polysorbate 20's effect was restricted to *P. bivia* and *P. anaerobius* which were suppressed by the three concentrations tested. Results indicated that the various fiber finishes tested effect the growth of obligate anaerobes while having little or no effect on facultative anaerobes.

D. Determination of Effect of Various Tampons on Vaginal Microflora

The in vitro effects of various tampon types on both facultative and obligate anaerobes were examined. Six bacterial isolates representing commonly isolated species from normal vaginal cultures were grown in a chemically defined medium (VDM) representing genital tract secretions (Geshnizgani, et al., *J. Clin. Micro.* 30:1323–1326 (1992)). The bacterial cultures were grown alone or in the presence of tampons of various compositions. Bacterial counts were determined at times 0, 24 and 48 hours after inoculation of the cultures and the results analyzed.

Culture Media VDM was prepared as outlined in Geshnizgani et al. (*J. Clin. Micro.* 30:1323–1326 (1992)) and 125 ml dispensed into screw capped Erlenmeyer flasks designed to hold 125 ml. The flasks were then placed into an anaerobic chamber for 72 hours prior to use to ensure that the media had been reduced. The solid media used for culturing obligately anaerobic species was prereduced brucella-base agar containing 5% sheep blood, and 0.01 g of both hemin and vitamin $K^1$ per liter (BMB). Tryptic soy agar containing 5% sheep blood (TSB) was used for recovery of facultative anaerobes.

Bacterial Isolates: The bacterial isolates used were taken from a frozen stock culture collection of vaginal isolates (Anaerobe Research Laboratory. Channing Laboratory, Boston, Mass.). The facultative species included *Staphylococcus aureus* (Smith 20), *Staphylococcus epidermidis* (Pyne 3), and *Escherichia coli* (TSS-4) while the obligately anaerobic species were *Lactobacillus acidophilus* (239-13), *Peptostreptococcus anaerobius* (TSS-23), and *Prevotella bivia* (1-17). The frozen stock cultures were subcultured onto either TSB or BMB and incubated aerobically at 35° C. or in an anaerobic chamber at 35° C., respectively. The cultures were examined for purity and Gram stains performed on each species. Flasks containing 125 ml of reduced VDM were inoculated with each bacterial isolate and incubated under the appropriate conditions for 24 to 48 hours. Five ml aliquots of each bacterial isolate were flash frozen in dry ice/ethanol and stored at −80° C. A frozen aliquot of each stock culture was thawed and serial 10-fold dilutions were made in phosphate buffered saline (PBS) to determine the total bacterial count.

Test Tampons: The test tampons were provided and coded by Tambrands, Inc. The tampons were sterilized with ethylene oxide at Dartmouth Hitchcock Medical Center, prior to use in these studies. Each tampon was aseptically cut into two equal pieces. The two pieces of each tampon were used as a duplicate set.

Experimental Design: For each species, duplicate flasks of reduced VDM containing the cut halves of the test tampons, the control tampon (100% cotton), and no tampon were prepared. The flasks were then inoculated with approximately $1\times10^4$ colony forming units per milliliter (CFU/ml) of the frozen inoculum. All flasks were incubated on a platform shaker (150 rpm) in an anaerobic chamber at 35° C. At times 0, 24 and 48 hours after inoculation, serial 10-fold dilutions of the growth medium from each test flask were made in PBS, plated onto TSB and BMB and incubated for 24 or 72 hours, respectively. Bacterial counts were determined and reported as $\log_{10}$ CFU/ml.

Example 5

Effect of Compositions on Vaginal Microflora

The effect of compositions on a woman's vaginal microflora can be quantified using the statistical model described in Lee, et al. (*Microbial Ecology in Health and Disease* 7, 235–240(1994)) which is incorporated by reference herein.

It was found in developing a predictive model of microbial concentrations that only a few of the variables tested were highly correlated with the total bacterial concentrations within the vaginal vault. A multiple regression model with backward elimination was used to identify pH and explanatory risk factors for the predictive analysis of total microbial concentrations. The explanatory risk factors used were: total aerobic bacterial concentration (designated "TAB"), Lactobacillus spp. concentration (designated "LAC"), Staphyloccus spp. concentration (designated "STP") and Prevotella spp. concentration (designated "PREV"). The following generalized estimating equation ("GEE") is used:

$$GEE = \text{logit } (p(t)) = B_0 + B_1 \times X_1(t) + B_2 \times X_2(t) + \ldots + Bk \times Xk(t) + e$$

where:

t=time

Y(t) denotes a dichotomous variable such that Y(t)=1 indicates that the vaginal ecosystem is abnormal and Y(t)=0 denotes a normal microbiota at time t.

(p(t))=probability $X_1(t)$=pH $X_2(t)$=STP $X_3(t)$=TAB $X_4(t)$=LAC $X_5(t)$=PREV, and e is the sampling error (typically about 3%).

The GEE model was then applied to the vaginal microbiota data set to yield the following equation: G=logit (p(r))=1.06−0.53×PH−0.84×STP+0.16×TAB+0.30×LAC−0.23×PREV. This links the logit of the probability of having abnormal microbial concentrations at time t with the corresponding pH and other explanatory risk factors.

The range for considering an individual calculated value to be normal is if the value of G is between 0 and 0.1. For the purposes of the present invention, the vaginal microflora is considered to not be disturbed if the calculated value according to the above equation is between 0 and less than or equal to about 0.15, and is more preferably between 0 and less than or equal to about 0.1.

The following oxygen inhibiting agents were tested for their effect on bacterial toxin production and bacterial growth: control (no inhibitor) 200; ascorbic acid (0.06%) 202; propyl gallate (0.1%) 204; delta-tocopherol (2.0%) 206; cysteine (0.1%) 208; N-acetyl-cysteine (0.2%) 210; beta-mercaptoethanol 212; thiodipropionic acid (0.02%) 214; potassium bisulfite (0.05%) 216; sodium bisulfite (0.05%) 218; caffeine (0.025%) 220; and glutathione (0.2%) 222. With the exception of potassium bisulfite all of the agents tested reduced toxin production.

The effect of these agents on bacterial growth was also determined as a percentage of control. Results are expressed in terms of final optical densities at $OD_{540}$ and are shown in Table 1.

TABLE 1

| $OD_{540}$ (Percentage of Control) | |
| --- | --- |
| Control (no inhibitor) | 100 |
| Ascorbic acid | 104 |
| Propylgallate | 74 |
| delta-tocopherol | 112 |
| Cysteine | 105 |
| N-acetyl cysteine | 89 |
| Beta-mercaptoethanol | 93 |
| Thiodipropionic acid | 99 |
| Potassium bisulfite | 91 |
| Sodium bisulfite | 64 |
| Caffeine | 93 |
| Glutathione | 117 |

The effect of glycerol plus ascorbic acid on TSST-1 promoter activity was determined. Ascorbic acid at percentages of 0.063%; 0.031%; 0.016%; and 0% was tested with glycerol at 0.6%, 0.4% and 0.2%. In all cases, promoter activity was reduced relative to the activity seen in controls.

This invention has been described in connection with a catamenial tampon but would also be applicable to other disposable absorbent articles, such as: medical bandages, especially nasal surgical packings, wound dressings, and other absorbent articles where reduction in toxic shock syndrome toxin production might be beneficial.

The disclosures of all patents, patent applications (and any patents which issue thereon, as well as any corresponding published foreign patent applications), and publications mentioned throughout this description, including the Background of the Invention section, are hereby incorporated by reference herein.

While particular embodiments of the present invention have been illustrated and described, it would be obvious to those skilled in the art that various other changes and modifications can be made without departing from the spirit and scope of the invention.

What is claimed is:

1. A tampon having additives that reduce toxic shock syndrome toxin (TSST-1) production without adversely affecting a wearer's vaginal flora, said tampon comprising: a combination of an effective amount of beta-mercaptoethanol and an effective amount of at least one surface active agent applied to: the surface of the absorbent tampon materials; the surfaces of the fibers comprising the tampon; the tampon applicator; or any combination of the foregoing, said effective amounts of said beta-mercaptoethanol and said surface active agent being sufficient to reduce the TSST-1 production of an *S. aureus* isolate by at least 50% in in vitro testing, and wherein said surface active agent is selected from the group consisting of: glycerol, polysorbate 40; polysorbate 60; polysorbate 80; PPG-5-laureth-5; PPG-8-stearate; polyethylene glycol; and polypropylene glycol.

2. The tampon of claim 1, wherein said surface active agent is glycerol.

3. The tampon of claim 1, wherein said surface active agent is selected from the group consisting of: polysorbate 40; polysorbate 60; polysorbate 80; PPG-5-laureth-5; and PPG-8-stearate.

4. The tampon of claim 1, wherein said surface active agent is selected from the group consisting of: polyethylene glycol; and polypropylene glycol.

5. A tampon having additives that reduce toxic shock syndrome toxin (TSST-1) production without adversely affecting a wearer's vaginal flora, said tampon comprising: a combination of an effective amount of N-acetylcysteine and an effective amount of at least one surface active agent applied to: the surface of the absorbent tampon materials; the surfaces of the fibers comprising the tampon; the tampon applicator; or any combination of the foregoing, said effective amounts of said N-acetylcysteine and said surface active agent being sufficient to reduce the TSST-1 production of an *S. aureus* isolate by at least 50% in in vitro testing, and wherein said surface active agent is selected from the group consisting of: glycerol; polysorbate 40; polysorbate 60; polysorbate 80; PPG-5-laureth-5; PPG-8-stearate; polyethylene glycol; and polypropylene glycol.

6. The tampon of claim 5, wherein said surface active agent is glycerol.

7. The tampon of claim 5, wherein said surface active agent is selected from the group consisting of: polysorbate 40; polysorbate 60; polysorbate 80; PPG-5-laureth-5; and PPG-8-stearate.

8. The tampon of claim 5, wherein said surface active agent is selected from the group consisting of: polyethylene glycol; and polypropylene glycol.

9. A method of reducing toxic shock syndrome toxin (TSST-1) production on an absorbent article, comprising, treating said absorbent article with:
   a) an effective amount of an oxygen inhibiting agent selected from the group consisting of N-acetylcysteine and beta-mercaptoethanol; and
   b) an effective amount of at least one surface active agent selected from the group consisting of: glycerol; polysorbate 40; polysorbate 60; polysorbate 80; PPG-5-laureth-5; PPG-8-stearate; polyethylene glycol; and polypropylene glycol;

wherein said effective amounts are sufficient to detoxify said toxin but do not adversely affect normal bacterial flora.

10. The method of claim 9, wherein said oxygen inhibiting agent is N-acetylcysteine.

11. The method of claim 10, wherein said surface active agent is glycerol.

12. The method of claim 10, wherein said surface active agent is selected from the group consisting of: polysorbate 40; polysorbate 60; polysorbate 80; PPG-5-laureth-5; and PPG-8-stearate.

13. The method of claim 10, wherein said surface active agent is selected from the group consisting of: polyethylene glycol; and polypropylene glycol.

14. The method of claim 9, wherein said oxygen inhibiting agent is beta-mercaptoethanol.

15. The method of claim 14, wherein said surface active agent is glycerol.

16. The method of claim 14, wherein said surface active agent is selected from the group consisting of: polysorbate 40; polysorbate 60; polysorbate 80; PPG-5-laureth-5; and PPG-8-stearate.

17. The method of claim 14, wherein said surface active agent is selected from the group consisting of: polyethylene glycol; and polypropylene glycol.

\* \* \* \* \*